(12) United States Patent
Argento

(10) Patent No.: US 6,648,856 B1
(45) Date of Patent: Nov. 18, 2003

(54) NEEDLE FOR MEDICAL AND/OR VETERINARY USE THAT INCLUDES AN EXTENSIBLE TELESCOPIC SYSTEM THAT COVERS THE NEEDLE AVOIDING ITS FUTURE USE

(76) Inventor: Jorge Luis Argento, San Martin 686 7° piso of. 72 - 1004, Capital Federal (AR)

( * ) Notice: Subject to any disclaimer, the term of this patent is extended or adjusted under 35 U.S.C. 154(b) by 0 days.

(21) Appl. No.: 09/080,726

(22) Filed: May 21, 1998

(30) Foreign Application Priority Data

May 27, 1997 (AR) .................................. P 97 01 02248

(51) Int. Cl.[7] .............................................. A61M 5/32
(52) U.S. Cl. ...................................... 604/192; 604/110
(58) Field of Search ................................ 604/192, 198, 604/187, 263, 110

(56) References Cited

U.S. PATENT DOCUMENTS

| | | | | |
|---|---|---|---|---|
| 4,747,831 A | * | 5/1988 | Kulli | 604/110 |
| 4,767,413 A | * | 8/1988 | Haber et al. | 604/198 |
| 4,813,426 A | * | 3/1989 | Haber et al. | 128/763 |
| 4,813,940 A | * | 3/1989 | Parry | 604/198 |
| 4,846,796 A | * | 7/1989 | Carrell et al. | 604/110 |
| 4,894,055 A | * | 1/1990 | Sudnak | 604/198 |
| 5,129,884 A | * | 7/1992 | Dysarz | 604/164 |
| 5,197,953 A | * | 3/1993 | Colonna | 604/110 |
| 5,242,420 A | * | 9/1993 | Martin | 604/198 |
| 5,246,428 A | * | 9/1993 | Falknor | 604/198 |
| 5,267,976 A | * | 12/1993 | Guerineau | 604/198 |
| 5,292,314 A | * | 3/1994 | D'Alessio et al. | 604/198 |
| 5,295,963 A | * | 3/1994 | Deeks | 604/110 |
| 5,295,975 A | * | 3/1994 | Lockwood, Jr. | 604/198 |
| 5,423,758 A | * | 6/1995 | Shaw | 604/110 |
| 5,554,122 A | * | 9/1996 | Emanuel | 604/110 |
| 5,637,092 A | * | 6/1997 | Shaw | 604/110 |
| 5,658,257 A | * | 8/1997 | Ryles | 604/195 |
| 5,674,203 A | * | 10/1997 | Lewandowski | 604/197 |
| 5,685,863 A | * | 11/1997 | Botich et al. | 604/198 |
| 5,688,241 A | * | 11/1997 | Asbaghi | 604/110 |
| 5,873,856 A | * | 2/1999 | Hjertman et al. | 604/117 |
| 5,935,113 A | * | 8/1999 | Dysarz | 604/263 |
| 6,096,005 A | * | 8/2000 | Botich et al. | 604/110 |
| 6,217,559 B1 | * | 4/2001 | Foster | 604/195 |

* cited by examiner

*Primary Examiner*—Manuel Mendez
(74) *Attorney, Agent, or Firm*—Pendorf & Cutliff

(57) ABSTRACT

NEEDLE FOR MEDICAL AND/OR VETERINARY USE; characterized by the fact of being constituted by two concentric cylindrical builds and a spring, which once assembled, they form an extensible telescopie system, that once activated, it covers the needle completely, forcing the person to throw it away definitively.

5 Claims, 2 Drawing Sheets

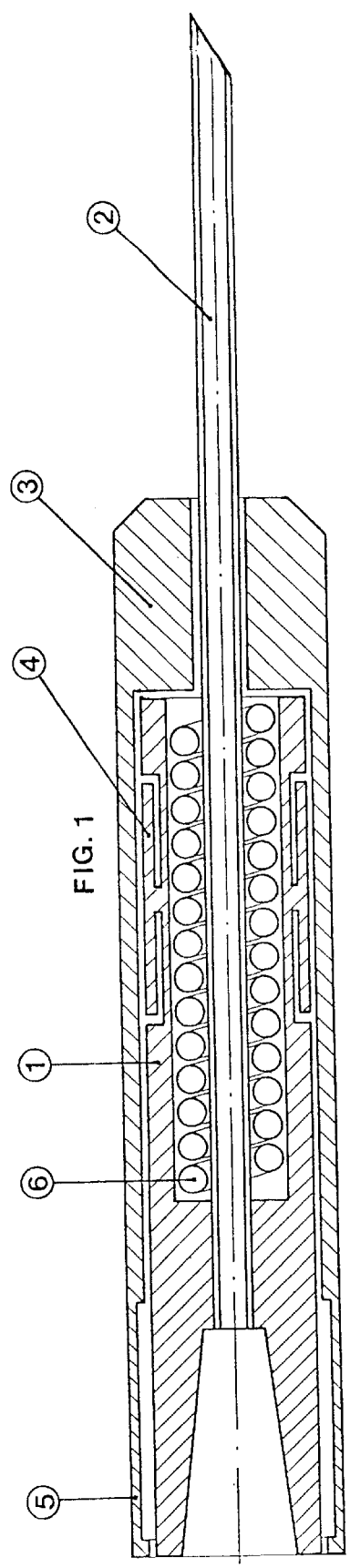
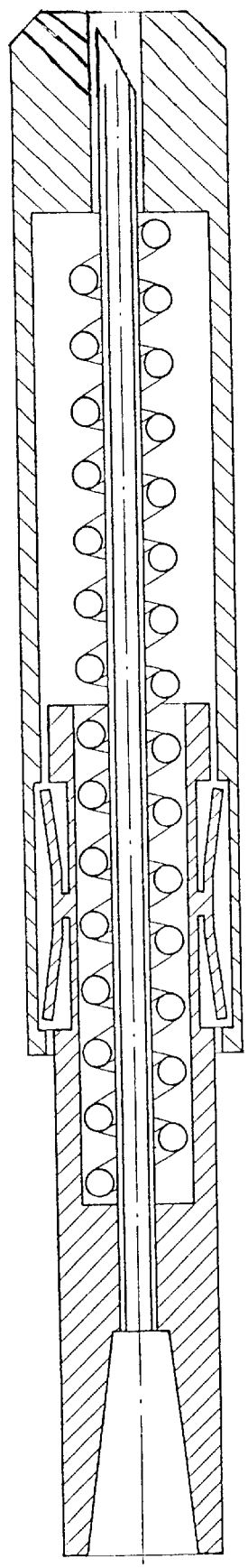

NEEDLE FOR MEDICAL AND/OR VETERINARY USE THAT INCLUDES AN EXTENSIBLE TELESCOPIC SYSTEM THAT COVERS THE NEEDLE AVOIDING ITS FUTURE USE

BACKGROUND OF THE INVENTION

This invention consists of a needle for medical and/or veterinary use that includes an extensible telescopic system propelled by a spring. Once this spring is activated, and due to the working of self-expansive flanges, it covers the needle completely avoiding its future use, forcing the user to throw it away definitively, and in that way, preventing the user and/or third parties from possible dangers, accidents or any risks.

Presently, it is well-known that the use of needles for the extraction of fluids from the human and/or animal body does not show any kind of protection in view of possible accidents that may occur as soon as the needle, full of fluids, is removed from the body, and until it is thrown away definitively. In view of the ignorance of the dangers of the fluids extracted, and once the due analysis are done, the person and/or third parties that are in charge of this activity run a very high risk as a result of such ignorance, since any risk or accident that could ever happen could be a great danger for their lives, such as it is the case of AIDS and hepatitis patients who must receive special attention, not only in their first consultation, but also in their future examinations.

At present, there is a popular use needle holder that consists of a container, generally on shelves, tabletops, or desks, whose main purpose is to hold the needle in its embedding with the syringe, and take the needle off, making the needle fall down inside the container.

It's true that this system makes possible a definitive elimination of the needle; however, it does not protect the user and/or third parties as soon as the needle is removed from the body and until it is introduced in the needle holder.

Therefore, the present invention prevents the user from any kind of risk as soon as the needle is removed from the body after fluid extraction, inasmuch as when the device is activated, the needle is completely covered by a cylindrical build; and due to the existence of self-expansive flanges, it is impossible that the cylindrical build goes backwards leaving the needle exposed. Hence, this mechanism forces the user to throw the needle away definitively; a procedure that is carried out with absolute security.

Besides, it is an outstanding feature the fact that the present device has an easy and practical realization; therefore, the present invention can be achieved at a very low cost of production, it can be easy acquired and it can also contribute to the elimination of legal actions with their consequent costs, and the attenuation of occupational accidents insurance policies.

All of these important characteristics of the invention and many other ones will be demonstrated in the following detailed description which will be done in accordance with the enclosed drawings that are included at the present as a mere example of the description above mentioned:

BRIEF DESCRIPTION OF THE DRAWINGS

FIGS. 1–4 are sectional views of the needle.

DESCRIPTION OF THE PREFERRED EMBODIMENT

Figure 3:
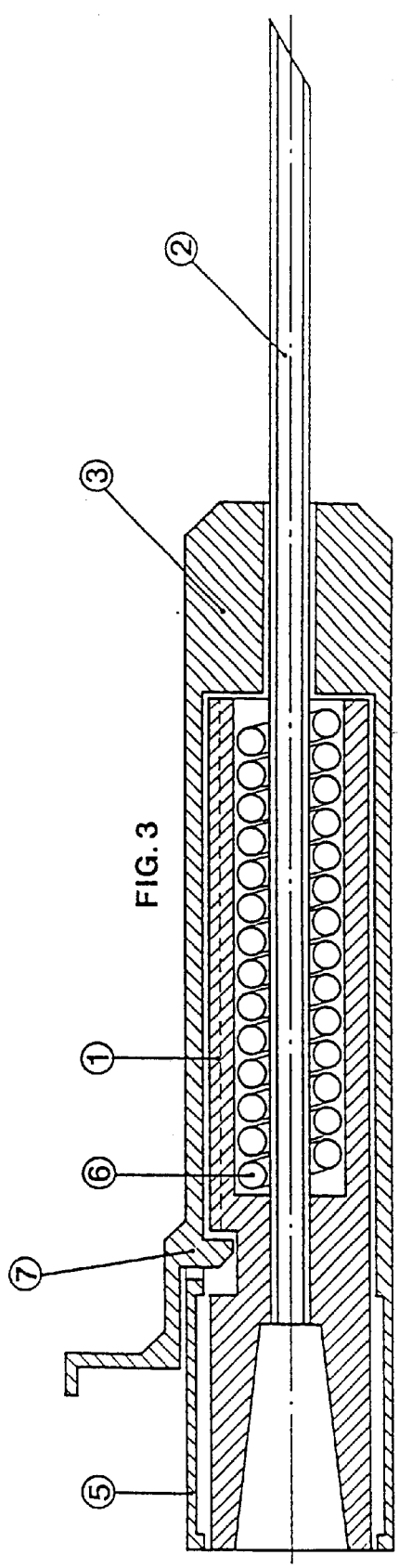

FIG. 1 is a device assembled with the inner cylindrical build (1) in which it can be observed that the build (1) has integral thereto longitudinally elongated self-expansive flanges (4), a compression and expansion spring (6) and a hypodermic needle (2) poking out from the device, making possible its future use for the extraction. The longitudinally elongated self-expansive flanges are made of a resilient material with its fore and rear ends in contact with the internal surface of the outer cylindrical build furthermore, it is shown the outer cylindrical build (3) before the shot.

FIG. 2 is the device after the shot in which it can be observed that the whole covering of the needle and the working of the self-expansive flanges getting stuck at the outer cylindrical build (3) according to the inner edge (5) when the telescopic system is activated by the spring. Further, the point of the syringe becomes embedded within a rectangular blind hole that terminated in a longitudinal channel with less depth and acts as a guide for the needle. Around the inner periphery of the outer cylindrical build is a cylindrical edge that allows free movement of the self-expansive flanges of the inner cylindrical build prior to getting stuck at the inner edge of the outer cylindrical build and before the shot.

Figure 4:
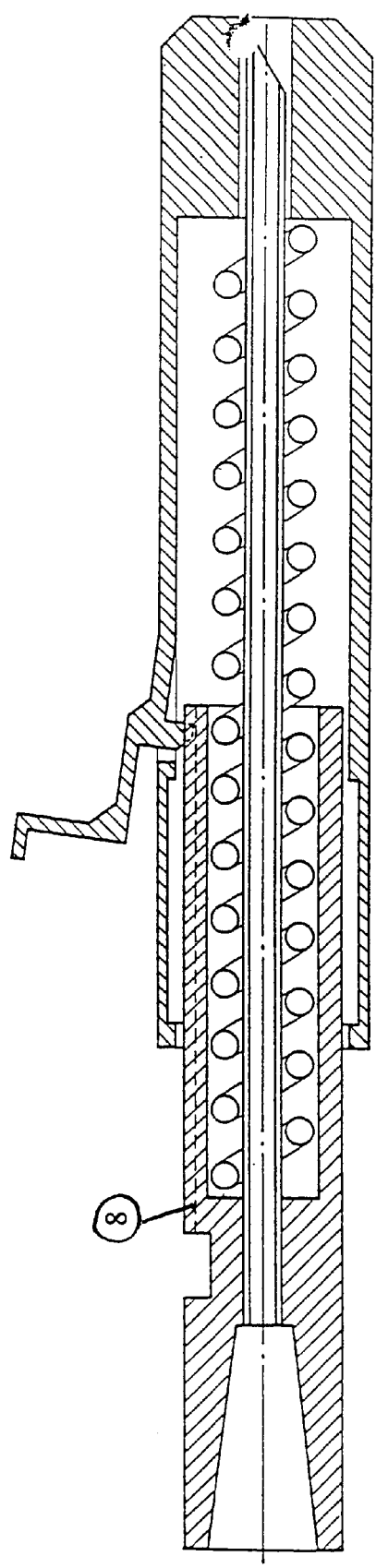

FIG. 3 is the device that is shown in a plane 90 degrees from the plane of FIGS. 1 and 2. In FIG. 3, the outer cylindrical build (3) is shown with a stuck and activation element. The stuck and activation element is shown as a trigger (7) that holds the outer cylindrical build (3) in position to cause the spring to be compressed, and control the operation of the needle. The trigger, when controlling the compression and expansion of the spring, is stuck in a rectangular blind needlecase of the inner cylindrical build (1) and stays there to allow the self-expansive flanges of the inner cylindrical build (1) to remain at rest or become locked at the inner edge (5) of the outer cylindrical build (1). The rectangular blind needlecase terminates in a longitudinal channel (8) of less deepness than a trigger edge. The longitudinal channel of the inner cylindrical build is in a plane 90 degrees from at least one of the self-expansive flanges shown in FIG. 2. FIG. 4 demonstrates the subsequent moment to the shot and the trigger stroke over the longitudinal channel.

Having described and defined the nature and scope of the present invention and the way it can be put into practice, it is declared to claim as of exclusive right and property:

1. A needle with an extensible telescopic system assembly for medical and/or veterinary use during body fluid extraction comprising:

two concentric cylindrical builds forming an inner cylindrical build and an outer cylindrical build;

a compression and expansion spring;

the inner cylindrical build having longitudinally elongated self-expansive flanges integral thereto, the longitudinally elongated self-expansive flanges are made of a resilient material with its fore and rear ends in contact with the internal surface of the outer cylindrical build;

the outer cylindrical build having an inner edge and a stuck and activation element;

the two concentric cylindrical builds and the compression and expansion spring are assembled to form an extensible telescopic system that is provoked by the stuck and activation element; and wherein activation of the compression and expansion spring of the extensible telescopic system after fluid extraction and a hypodermic needle is removed from the body during use causes the longitudinally elongated self-expansive flanges to work and cause the outer cylindrical build to cover the hypodermic needle thereof and making it impossible to re-expose the needle.

2. The needle for medical and/or veterinary use during body fluid extraction, in accordance with claim 1, wherein, before the shot and prior to activation of the extensible telescopic system around the hypodermic needle the self expansive flanges of the inner cylindrical build remain at rest while the outer cylindrical build encases the inner cylindrical build causing the spring to be compressed and the inner cylindrical build embodying the hypodermic needle therein allows the hypodermic needle to poke out from the outer cylindrical build.

3. The needle for medical and/or veterinary use during body fluid extraction, in accordance with claim 1, wherein the self expansive flanges when working after a shot where fluid extraction has occurred, gets locked at the inner edge of the outer cylindrical build when the telescopic system around the hypodermic needle is activated by the expansion of the compression and expansion spring, and the point of the syringe becomes embedded within a rectangular blind hole that terminated in a longitudinal channel with less depth and acts as a guide for the needle.

4. A The needle for medical and/or veterinary use during body fluid extraction, in accordance with claim 1, wherein, the stuck and activation element of the outer cylindrical build is a trigger on a side thereof to hold the spring compressed and controlling the operation of the needle, and the inner cylindrical build has a corresponding rectangular blind needle case that terminated in a longitudinal channel of less depression than a trigger edge for the trigger to stay, the longitudinal channel is on another side of the inner cylindrical build that is in a plan 90 degrees from the self-expansive flanges.

5. The needle for medical and/or veterinary use during body fluid extraction, in accordance with claim 4, wherein, the outer cylindrical build further having an inner periphery surrounded by a cylindrical edge therearound to allow free movement of the self-expansive flanges of the inner cylindrical build prior to getting locked at the inner edge of the outer cylindrical build when the compression and expansion spring is expanded.

* * * * *